(12) United States Patent
Kornbluth et al.

(10) Patent No.: US 12,198,484 B2
(45) Date of Patent: Jan. 14, 2025

(54) SYSTEMS AND METHODS FOR DETECTING WINDSHIELD CRACKS

(71) Applicant: Robert Bosch GmbH, Stuttgart (DE)

(72) Inventors: Mordechai Kornbluth, Brighton, MA (US); Soo Kim, Arlington, MA (US); Jonathan Mailoa, Cambridge, MA (US); Charles Tuffile, Swansea, MA (US); Karim Gadelrab, Boston, MA (US); Georgy Samsonidze, San Francisco, CA (US)

(73) Assignee: Robert Bosch GmbH (DE)

( * ) Notice: Subject to any disclaimer, the term of this patent is extended or adjusted under 35 U.S.C. 154(b) by 771 days.

(21) Appl. No.: 17/405,384

(22) Filed: Aug. 18, 2021

(65) Prior Publication Data
US 2023/0055880 A1 Feb. 23, 2023

(51) Int. Cl.
| | |
|---|---|
| G07C 5/08 | (2006.01) |
| B60J 1/02 | (2006.01) |
| C09D 1/00 | (2006.01) |
| C09D 5/24 | (2006.01) |
| G01N 21/958 | (2006.01) |
| G01N 27/04 | (2006.01) |
| G01N 27/20 | (2006.01) |
| G01N 33/38 | (2006.01) |

(52) U.S. Cl.
CPC .............. *G07C 5/0825* (2013.01); *B60J 1/02* (2013.01); *C09D 1/00* (2013.01); *C09D 5/24* (2013.01); *G01N 21/958* (2013.01); *G01N 27/041* (2013.01); *G01N 27/20* (2013.01); *G01N 33/386* (2013.01); *G07C 5/0833* (2013.01)

(58) Field of Classification Search
CPC .... G01N 33/386; G01N 27/20; G01N 27/041; G01N 21/958; C09D 5/24; C09D 1/00; B60J 1/02; G07C 5/0825; G07C 5/0833
USPC .......................................................... 219/510
See application file for complete search history.

(56) References Cited

U.S. PATENT DOCUMENTS

| | | | | |
|---|---|---|---|---|
| 4,565,919 A | * | 1/1986 | Bitter | ................ B32B 17/10174 |
| | | | | 219/203 |
| 4,808,799 A | * | 2/1989 | Schave | ................ H05B 1/0236 |
| | | | | 219/203 |

(Continued)

FOREIGN PATENT DOCUMENTS

| | | | | |
|---|---|---|---|---|
| CN | 110268253 A | * | 9/2019 | ........... B60R 25/305 |
| EP | 1648200 A1 | | 4/2006 | |

(Continued)

*Primary Examiner* — Jimmy Chou
(74) *Attorney, Agent, or Firm* — Dickinson Wright PLLC (57) ABSTRACT

Systems and methods are disclosed for detecting a crack in an automotive windshield and alerting a user of the same. This can allow the user to repair the crack before the user might otherwise detect the crack by his/her own visual inspection. The windshield can be provided with emitters configured to emit signals (e.g., sound, light, etc.) and corresponding detectors configured to detect the emitted signals. Signal profiles or signatures can be stored that represent normal measurements when there is no crack. Upon detecting a signal signature that deviates from the stored normal signal signatures, the system can notify the user of a potential crack in the windshield. The system can also determine the location of the crack based upon which of the detectors detect a change in the detected signal.

10 Claims, 5 Drawing Sheets

(56) References Cited

U.S. PATENT DOCUMENTS

| | | | | |
|---|---|---|---|---|
| 4,829,163 A * | 5/1989 | Rausch | | H02H 5/10 |
| | | | | 219/547 |
| 4,894,513 A * | 1/1990 | Koontz | | B32B 17/10036 |
| | | | | 219/203 |
| 4,902,875 A * | 2/1990 | Koontz | | H05B 3/86 |
| | | | | 219/203 |
| RE33,343 E * | 9/1990 | Bitter | | H02H 5/10 |
| | | | | 219/203 |
| 4,994,650 A * | 2/1991 | Koontz | | B32B 17/10174 |
| | | | | 219/505 |
| 5,089,687 A * | 2/1992 | Bartrug | | B32B 17/10293 |
| | | | | 219/541 |
| 5,434,384 A * | 7/1995 | Koontz | | B60S 1/048 |
| | | | | 219/547 |
| 5,543,601 A * | 8/1996 | Bartrug | | B32B 17/10174 |
| | | | | 338/322 |
| 5,824,994 A * | 10/1998 | Noda | | H05B 3/84 |
| | | | | 219/541 |
| 6,020,576 A * | 2/2000 | Shiah | | G01K 1/14 |
| | | | | 361/87 |
| 6,140,622 A * | 10/2000 | Goings | | H05B 3/34 |
| | | | | 219/506 |
| 6,794,882 B2 * | 9/2004 | Jessup | | B60R 25/1004 |
| | | | | 219/509 |
| 9,076,277 B2 * | 7/2015 | Delong | | G07C 5/085 |
| 10,739,292 B1 * | 8/2020 | Melcher | | H05B 3/12 |
| 2001/0003336 A1 * | 6/2001 | Abbott | | F27D 11/02 |
| | | | | 118/724 |
| 2006/0186104 A1 * | 8/2006 | Winter | | B32B 17/10036 |
| | | | | 219/203 |
| 2006/0186105 A1 * | 8/2006 | Voeltzel | | B32B 17/10174 |
| | | | | 219/203 |
| 2017/0013679 A1 * | 1/2017 | Tomar | | H05B 3/84 |
| 2018/0029563 A1 * | 2/2018 | Beloe | | B60H 1/00785 |
| 2021/0041542 A1 * | 2/2021 | Shepard | | G01S 17/89 |

FOREIGN PATENT DOCUMENTS

| | | | | |
|---|---|---|---|---|
| GB | 2536238 A | * | 9/2016 | B60S 1/02 |
| JP | 2019060664 A | | 4/2019 | |
| WO | WO-2016142412 A1 | * | 9/2016 | B60H 1/00785 |
| WO | WO-2022264115 A1 | * | 12/2022 | B60S 1/0837 |

\* cited by examiner

SYSTEMS AND METHODS FOR DETECTING WINDSHIELD CRACKS

TECHNICAL FIELD

The present disclosure relates to systems and methods for detecting windshield cracks.

BACKGROUND

Automotive windshields are vital to safe driving, requiring a material that is both robust and transparent. Additional features to prevent sun glare (e.g., polarization, coatings, etc.) and fogging (e.g., heating) are often present, and add to the cost of the windshield.

One main point of failure of an automotive windshield occurs when an object such as a stone or rock impacts the windshield. This is especially true when driving at fast speeds on highways. These risks are even greater on unpaved roads or when driving behind construction vehicles that may be carrying gravel or the like. Such objects impacting the windshield can cause cracks, chips or the like to appear on the windshield. Other causes of cracks include extreme temperature fluctuations, hail, debris (e.g, nuts) falling from trees, and even golf balls or baseballs. Cracks can start off small and even unnoticed by the owner/driver of the automobile. But over time the cracks can grow in size due to temperature or pressure fluctuations.

Cracks in the windshield are not only cosmetically unsightly, but are also dangerous because they can impair vision and can lead to greater damage if the vehicle was later involved in a crash. It is therefore important to remedy windshield cracks as early as possible.

SUMMARY

In one embodiment, a system for detecting and notifying a user of a crack in an automotive windshield is provided. The system includes a plurality of emitters located at a first region of a windshield and configured to emit signals across at least a portion of the windshield. The system includes a plurality of detectors located at a second region of the windshield and configured to detect the signals after being transmitted across the portion of the windshield. The system includes at least one processor coupled to a memory and programmed to: (i) store a plurality of signal signatures into the memory, wherein the signal signatures represent qualities of the signals emitted by the emitters as detected by the detectors, (ii) instruct the plurality of emitters to emit a new signal across the portion of the windshield, (iii) compare a signal signature of the new signal with the signal signatures stored in the memory, and (iv) notify a user of a crack in the windshield in response to the signal signature of the new signal deviating from the signal signatures stored in memory.

In one embodiment, a method of detecting a crack in a windshield and notifying a user regarding the crack is provided. The method includes: emitting a first plurality of signals across at least a portion of the windshield from emitters located at a first region of the windshield; detecting the first plurality of signals via detectors located at a second region of the windshield; processing the first plurality of signals received by the detectors to derive first signal signatures; storing the first signal signatures in memory; emitting a second plurality of signals from the emitters; detecting the second plurality of signals via the detectors; processing the second plurality of signals received by the detectors to derive second signal signatures; comparing the second signal signatures with the first signal signatures; and notifying a user regarding a presence of a crack in the windshield in response to the second signal signature deviating from the first signal signatures.

In one embodiment, a system for detecting and notifying a user of a crack in an automotive windshield is provided. The system includes a windshield having a layer of a transparent conducting oxide (TCO). The system includes an array of electrical contacts disposed along the TCO and configured to detect voltage or current therebetween, wherein the electrical contacts are electrically interconnected within the windshield. The system includes at least one processor programmed to: detect a change in the voltage or current between at least two of the electrical contacts; determine a presence of a crack in the windshield based on the change in the voltage or current; and determine a location of the crack on the windshield based on a corresponding location of the at least two of the electrical contacts.

DETAILED DESCRIPTION

Embodiments of the present disclosure are described herein. It is to be understood, however, that the disclosed embodiments are merely examples and other embodiments can take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the embodiments. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

References are made in this disclosure to cracks in automotive windshields. It should be understood that a "crack" can come in many different shapes, types, and sizes. Unless otherwise noted, the term "crack" should not be limited to only a certain type of visible damage made to the windshield. Common types of cracks on windshields include chips, craters, horseshoe cracks, star cracks, bullseye, straight line, and spider webs. These types of damage to windshields are often caused by debris (e.g., stones) making contact with the windshield at high forces or velocities. It should be understood that references made herein to "crack" are intended to cover at least these types of damages.

Automotive windshields are important for safe driving. They need to be transparent, but also strong enough to resist damage from impact with external objects. One main point of failure of an automotive windshield occurs when an object such as a stone or rock impacts the windshield. This is especially true when driving at fast speeds on highways. These risks are even greater on unpaved roads or when driving behind construction vehicles that may be carrying gravel or the like. Such objects impacting the windshield can cause cracks to appear on the windshield.

Cracks in the windshield can start small, oftentimes undetectable by the naked eye. Even if visibly detectable, cracks may originate in a location on the windshield that the driver or passenger does not look at often enough to realize the crack is present. If not repaired soon, the crack can grow larger, which further degrades the appearance and safety of the windshield. And, bigger cracks are typically more expensive to repair. Some cracks can grow large enough to warrant a replacement of the entire windshield. It is imperative to recognize and repair the crack as early as possible.

Figure 1:
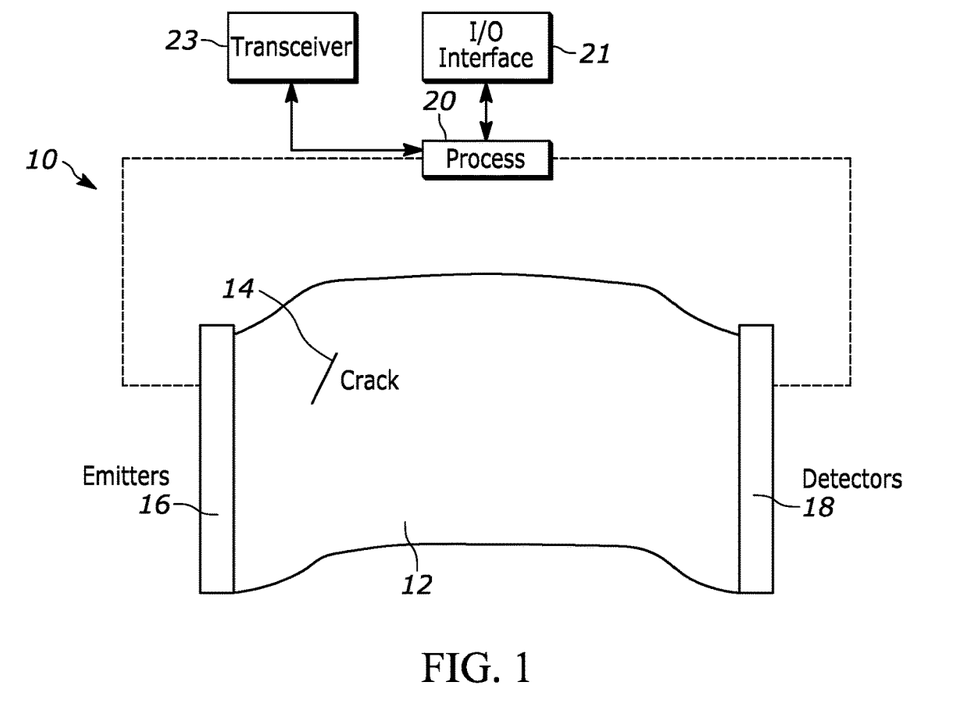
FIG. 1 is a schematic of a windshield and an associated system for detecting cracks on the windshield, according to an embodiment.

Therefore, according to various embodiments disclosed herein, systems and methods of detecting a crack in the windshield and notifying a user of the same are provided. An example of a system 10 for detecting a crack in the windshield is illustrated in FIG. 1. A windshield is generally shown at 12, having a crack 14 thereon. While the crack 14 is visible in FIG. 1, it should be understood that this may be only for illustration purposes only; in reality, the crack 14 may be so small as to not be visible or noticed by an occupant or driver of the vehicle. The crack may be as small as 0.1 millimeters (mm), or as large as 50 centimeters (cm). In certain embodiments, the system is configured to detect a crack between 0.1 mm and 30 cm. Also, the location of the crack 14 can vary, and is not limited to only the location shown in FIG. 1.

The system 10 includes one or more emitters 16 located at one side of the windshield 12, and one or more detectors 18 located at an opposite side of the windshield. The emitters 16 and detectors 18 can be located on opposite lateral sides of the windshield 12, for example adjacent the vehicle's A-pillar. Associated wires and electrical connectors can be disposed within or adjacent the A-pillar on one or either side of the windshield 12. In another embodiment, the emitters 16 and detectors 18 are each on both sides of the windshield 12 such that each side of the windshield includes both an emitter 16 and a detector 18. The emitters 16 and detectors 18 may also be on the upper or lower bounds of the windshield 12. In short, the emitters 16 and detectors 18 can be located at any location about the periphery of the windshield, or in some embodiments the detectors may be within the windshield as will be described more below.

The emitters 16 and/or the detectors 18 may be connected to a processor 20. The processor 20 may also generally be referred to as a controller, and can be one or more of a processor or controller capable of not only controlling the emitters 16, but receiving information from the detectors, processing the information, and outputting instructions to deliver a notification to the driver in response to a determined crack in the windshield. In this disclosure, the terms "controller" and "system" may refer to, be part of, or include processor hardware (shared, dedicated, or group) that executes code and memory hardware (shared, dedicated, or group) that stores code executed by the processor hardware. The code is configured to provide the features of the controller and systems described herein. In one example, the controller may include a processor, memory, and non-volatile storage. The processor may include one or more devices selected from microprocessors, micro-controllers, digital signal processors, microcomputers, central processing units, field programmable gate arrays, programmable logic devices, state machines, logic circuits, analog circuits, digital circuits, or any other devices that manipulate signals (analog or digital) based on computer-executable instructions residing in memory. The memory may include a single memory device or a plurality of memory devices including, but not limited to, random access memory ("RAM"), volatile memory, non-volatile memory, static random-access memory ("SRAM"), dynamic random-access memory ("DRAM"), flash memory, cache memory, or any other device capable of storing information. The non-volatile storage may include one or more persistent data storage devices such as a hard drive, optical drive, tape drive, non-volatile solid-state device, or any other device capable of persistently storing information. The processor may be configured to read into memory and execute computer-executable instructions embodying one or more software programs residing in the non-volatile storage. Programs residing in the non-volatile storage may include or be part of an operating system or an application, and may be compiled or interpreted from computer programs created using a variety of programming languages and/or technologies, including, without limitation, and either alone or in combination, Java, C, C++, C #, Objective C, Fortran, Pascal, Java Script, Python, Perl, and PL/SQL. The computer-executable instructions of the programs may be configured to, upon execution by the processor, inform the vehicle owner or operator of a presence of a crack in the windshield so that the owner or operator is made aware of the crack as early as possible for swift repair.

Implementations of the subject matter and the operations described in this specification can be implemented in digital electronic circuitry, or in computer software embodied on a tangible medium, firmware, or hardware, including the structures disclosed in this specification and their structural equivalents, or in combinations of one or more of them. Implementations of the subject matter described in this specification can be implemented as one or more computer programs embodied on a tangible medium, i.e., one or more modules of computer program instructions, encoded on one or more computer storage media for execution by, or to control the operation of, a data processing apparatus. A computer storage medium can be, or be included in, a computer-readable storage device, a computer-readable storage substrate, a random or serial access memory array or device, or a combination of one or more of them. The computer storage medium can also be, or be included in, one or more separate components or media (e.g., multiple CDs, disks, or other storage devices). The computer storage medium may be tangible and non-transitory.

A computer program (also known as a program, software, software application, script, or code) can be written in any form of programming language, including compiled languages, interpreted languages, declarative languages, and procedural languages, and the computer program can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, libraries, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., a field programmable gate array ("FPGA") or an application specific integrated circuit ("ASIC"). Such a special purpose circuit may be referred to as a computer processor even if it is not a general-purpose processor.

The processor 20 may be in communication with an associated vehicle transceiver for delivery and receipt of data and commands from a remote server (e.g., the cloud) as will be described further below. The processor 20 and/or associated controller is configured to operate the emitters 16, detect the signals emitted from the emitters 16 via detectors 18, process the associated signals from the detectors 18, and send associated alerts or information to the vehicle's owner about the presence of a crack in the windshield based on the processed information. As such, the processor 20 may be in communication with an associated input/output (I/O) interface 21 configured to display the notification of a presence of the crack. Non-limiting examples of an I/O interface 21 includes a vehicle display, a vehicle infotainment system, a mobile device such as a smartphone, audible devices such as vehicle speakers, and the like. The notification sent to the user regarding the detected presence of a crack may be, without limitation, through SMS, email, phone call, smartphone or smartwatch push notification, or lights or sounds directly within the vehicle.

The processor can receive and execute software applications, data and/or commands transmitted over a local network interface within the vehicle. The processor can also independently execute locally stored applications. However, in other embodiments, the system 10 is capable of communicating the data as detected from the detectors 18 to a remote server, such as the cloud as will be described in an embodiment below. As such, the processor 20 can be connected to a transceiver 23 configured for wired and/or wireless communication (e.g., a Wi-Fi transceiver, a Bluetooth transceiver, a cellular transceiver, a satellite transceiver, a GPS or SPS receiver, etc.). The transceiver 23 can include transceiver circuitry configured to transmit and/or receive information (e.g., data from the sensors disclosed herein) and can include a wireless communications interface (e.g., Bluetooth, Wi-Fi, Wi-Fi Direct, Long-Term Evolution (LTE) Direct, etc.) such as a wireless transceiver and associated hardware (e.g., an RF antenna, a MODEM, a modulator and/or demodulator, etc.).

Figure 2:
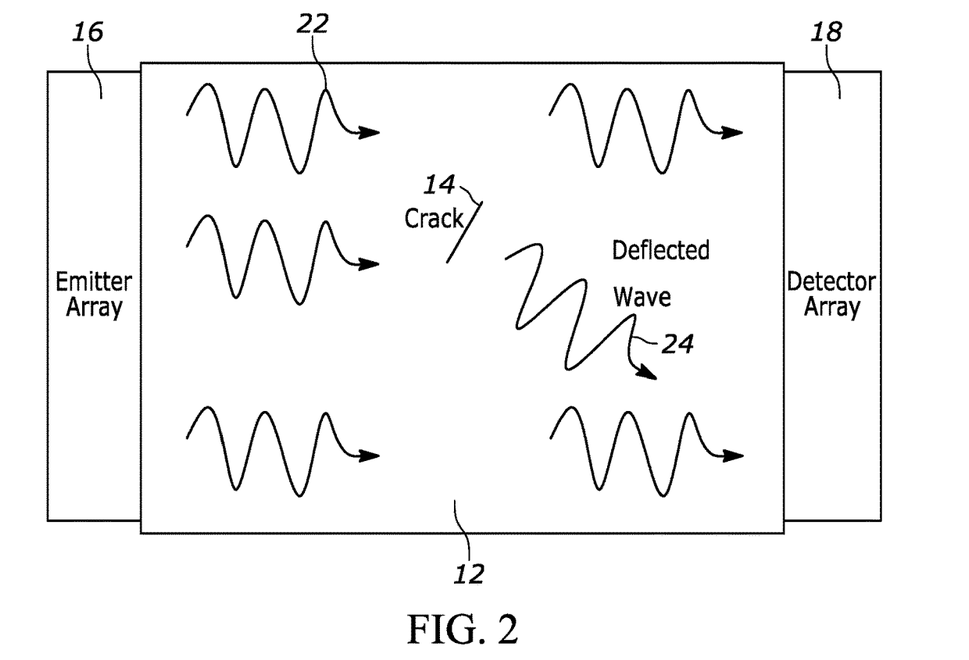
FIG. 2 is a schematic of emitted waves sent across the windshield for detecting cracks therein, according to an embodiment.

In general, the system can operate as follows according to an embodiment. Referring to FIG. 2, an array of emitters 16 can emit signals or waves 22 to be detected by a corresponding array of detectors 18. The signals or waves may be optical signals, acoustic signals, electrical signals, and the like which will be described further below. In normal operation with no cracks in the windshield, the signals propagate from the emitters 16 and are detected by the detectors 18 in normal fashion. In other words, the signal received by detectors 18 are consistent over time. The patterns of the signals or signal signatures received by the detectors 18 can be trained or stored as "normal" operation. In the presence of a crack 14, however, one or more of the signals is distorted, shown at wave 24. The detectors 18 detect this abnormality in the received signals, and the processor can correspondingly alert the driver of the presence of the crack 14 according to the teachings provided herein.

Figure 3:
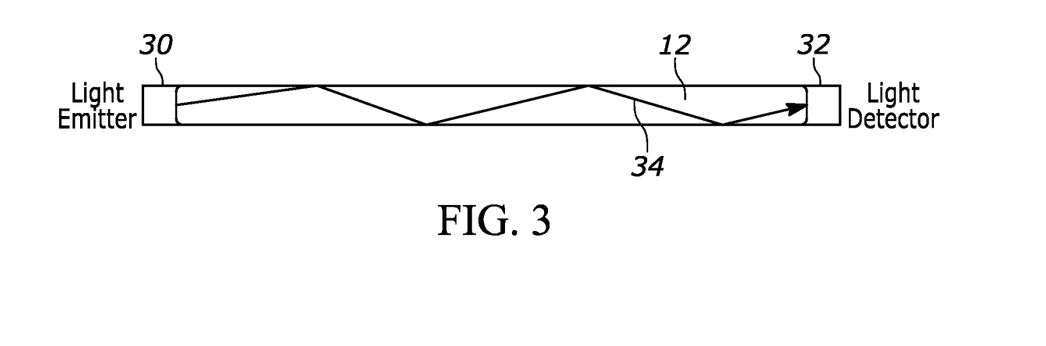
FIG. 3 is a cross-sectional schematic of the windshield with light reflected therein for detecting cracks optically, according to an embodiment.

FIG. 3 illustrates one embodiment of the emitters; in this example, the emitters are light emitters 30. The light emitters 30 may include one or more light source such as a light-emitting diode (LED) emitting light at certain wavelengths (e.g., infrared) that are undetectable to the human eye. The light emitters 30 may be located on one lateral side of the windshield 12. Corresponding light detectors 32 may be located on the opposite lateral side of the windshield 12 and are configured to detect or sense the light emitted from the light emitters 30. The light detectors 32 may include, for example, one or more photoresistors or photodiodes.

Light 34 emitting from the light emitters 30 can reflect within the windshield 12 until it is received at and detected by the light detectors 32. In one embodiment, the orientation and angle of the light emitters 30 is such that the light 34 can travel through total internal reflection (TIR) within the windshield 12; the light emitters emit light at an angle less than the critical angle of the windshield 12. This causes the emitted light waves to reflect completely within the boundary of the windshield where it can be detected by the detectors 32 on the other side of the windshield 12. The processor and associated memory connected to the detectors 32 can store the light signature detected by the detectors 32 into memory, thereby learning the light signatures associated with an unbroken windshield. In other words, the system can be provided with a "baseline" of what a light signature is sensed to look like under normal conditions. The presence of a crack in the windshield 12 scatters the light in a way that disturbs the light signature detected by the detectors 32. If the pattern of light or light signature detected by the detectors 32 deviates from the established baseline by a certain threshold, the system can determine that a crack is present in the windshield 12.

An advantage of this system is that due to the total internal reflection taking place in the windshield 12, there is less noise affecting the light signal that might otherwise be caused due to dirt or rain on the outer surface of the windshield. Since the light stays reflected within the windshield, disturbances from outside the windshield will not impact the pattern of the light as detected by the detectors 32 in a way that would cause the system to inadvertently output a signal indicating a crack in the windshield 12.

Optical detection of cracks can also be performed utilizing a camera. In particular, a camera mounted inside the vehicle can capture images of the windshield during operation, for example at constant or given time intervals. The camera may be the same camera that is also used to track the road for autonomous driving. The connected processor can compare the images over time, and if there are distortions to the windshield, the system can alert the driver of a potential crack in the windshield. This system can be utilized in a machine-learning environment using the teachings described herein as an example.

In another embodiment, the crack detection is performed acoustically. The emitters 16 may include one or more audio emitters, and the detectors 18 may include one or more audio detectors or receptors. Again, the audio emitters and audio detectors may be placed around the periphery of the windshield. The audio emitters and audio detectors may be configured to emit and detect sound of a given frequency. In one embodiment, the frequency is between 10 and 100 hertz (Hz). This can match typical automotive engine frequencies. If a crack is formed on the windshield 12, the sound will scatter in a way unlike in an undamaged windshield. In other words, the sound detectors may be coupled to the processor and associated memory whereby the system may learn or be programmed with an established baseline of a sound signature as detected by the detectors; the presence of a crack causes the signal detected by the sound detectors to depart from the established baseline, thereby causing the system to issue an alert to the user of the presence of a crack.

The system may also include a temperature sensor coupled to the windshield and the processor. This allows correction for temperature-caused fluctuations in the received sound signals. The temperature of the windshield may cause the sound detected by the detectors to change compared to the established baseline. Therefore the system may be compensated by using a temperature sensor so that as the sound signature differs with altering temperatures, the system is able to account for this knowledge. In addition or alternative to the temperature sensor coupled to the windshield, the system may use already-existing temperature sensors in the vehicle cabin or atmospheric (external) temperature sensors. A look-up table may be used that correlates a certain sound signature with a given temperature as the established baseline sound signature for an undamaged windshield.

In another embodiment, the acoustic sensors are patterned across the windshield, similar to the embodiment illustrated in FIG. 5 that is further described below. Each acoustic sensor can be an electroactive polymers (EAP) assembly which create a voltage change upon mechanical acoustic perturbations, which can then be detected by a corresponding voltage sensor. Examples of materials used in the EAP assembly would include silicone, polyurethane, acrylate, hydrocarbon, rubber, olefin copolymer, polyvinylidene fluoride copolymer, fluroroelastomer, styrenic copolymer, and adhesive elastomer. Each EAP assembly can be of the structure disclosed in U.S. patent application Ser. No. 16/897,929 titled SYSTEMS FOR WATER DECALCIFICATION which is incorporated herein by reference in its entirety. The EAPs may be embedded within the windshield, e.g., located within the outer surfaces of the windshield.

Figure 4:
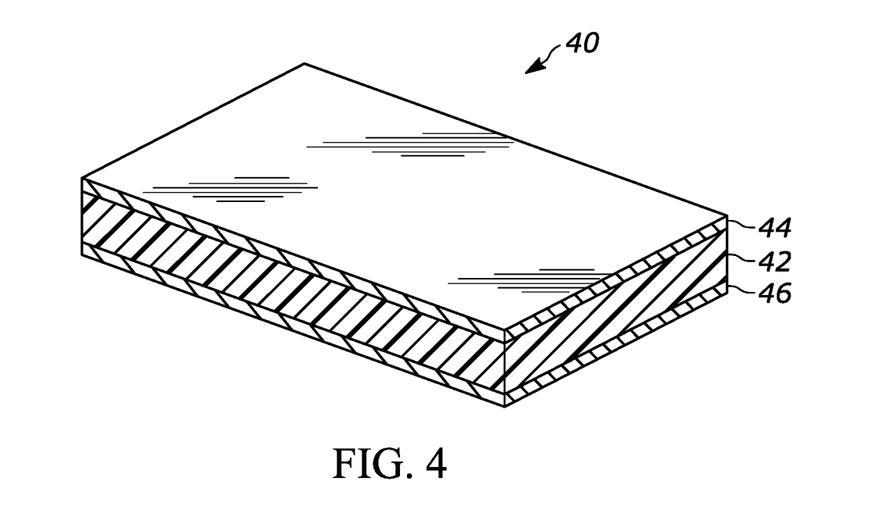
FIG. 4 is a schematic of an example of an acoustic sensor, in this case an electroactive polymer (EAP) according to an embodiment.

FIG. 4 illustrates on example of an EAP assembly 40 that can be used for acoustic detection of a windshield crack. Each EAP assembly 40 can be placed within or adjacent the windshield such that sound waves transmitting through the windshield are detected by the EAP assembly 40. Each EAP assembly 40 includes an EAP layer 42 (e.g., an electroactive polymer) situated between a first electrode 44 and a second electrode 46. The EAP layer 42 may have a thickness in a range of 10 µm to 100 µm. In addition, each of the first and second electrodes, 44 and 46, may have a thickness in a range of 100 nm to 1 µm. The dimensions (i.e. size and thickness) and the crystalline structures of the EAP layer 42 may be adapted to afford ultrasound vibrational energies according to applications of the EAP assembly 40. The first and second electrodes, 44 and 46, may be in electrical communication with an electrical source (not shown) such that an electrical voltage can be applied to the first and second electrodes, 44 and 46. In one embodiment, the electrical source may be an electrical grid dispersed within or adjacent the windshield. In another embodiment, the electrical source may be a battery. In yet another embodiment, the electrical source may be wirelessly coupled to the first and second electrodes, 44 and 46. Referring to FIG. 5 described below, the EAP assemblies can be patterned across the windshield similar to the electrodes illustrated and described with reference to that Figure.

The EAP layer 42 of the EAP assembly 40 may include at least one EAP film. The at least one EAP film may deform (i.e. physical changes in size and/or shape) under an influence of an electrical voltage applied to the first and second electrodes, 44 and 46. The deformation may lead to the generation of ultrasound vibrational energies. Removing the electrical voltage may subsequently allow the at least one EAP film to return to an original state (i.e. no deformation).

In another embodiment, cracks in the windshield can be detected via resistive detection. The windshield 12 may be coated with a transparent conducting oxide (TCO) with a chemical formula such as $M_xZnO_{1+y}$ (where M=Al and/or Ga; x is between 0 and 1, and y is between −1 and 1) or $M_xTiO_{2+y}$ (where M=Sb and/or W; x is between 0 and 1, and y is between −1 and 1) or $M_xSnO_{2+y}$ (where M=Sb, F, and/or In; x is between 0 and 1, and y is between −1 and 1. Electrical contacts may be dispersed within or adjacent the TCO, adjacent to an outer or inner surface of the windshield. The TCO may be patterned similar to the illustration of the electrodes and wires disclosed herein rather than coating a TCO over the entire windshield. The TCO pattern may be attached on the sides of the windshield to further electrical contacts that create voltage differential between the electrical contacts. The voltage or current differential measurements can be between two points of the TCO pattern, or between two points on the edges of the windshield, which can identify the crack location. The electrical contacts can be coupled to the processor for measurement and signal processing. The measurement of voltage or current can be taken between the contacts. By using a transparent conductive material, the driver's vision is not obstructed in a way that conventional electrodes and wires may obstruct the vision.

Figure 5:
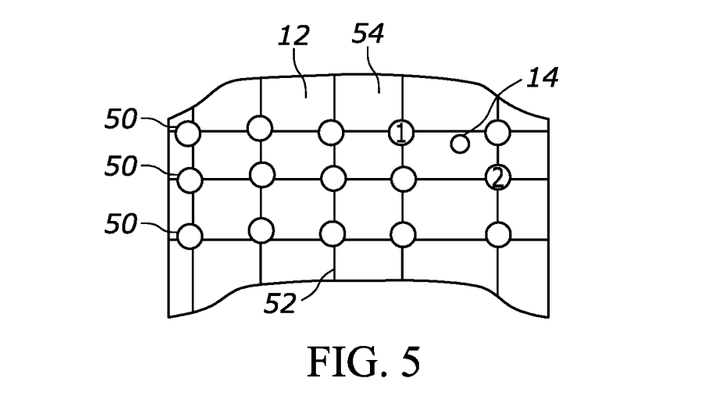
FIG. 5 is a schematic of the windshield illustrating an array of electrodes for detecting cracks via electrical resistance, according to an embodiment.
Figure 6:
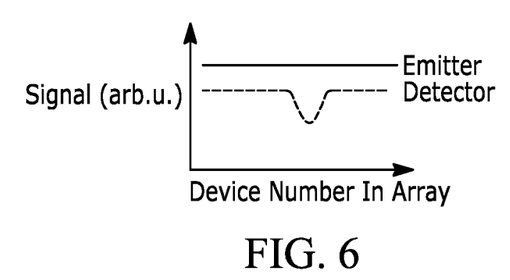
FIG. 6 is an example of a signal change in the electrodes during detection of a crack, according to an embodiment.

FIG. 5 illustrates a schematic of this embodiment. Referring to FIG. 5, the windshield 12 is equipped with a plurality of electrical contacts 50 (e.g., electrodes) disbursed throughout the windshield 12. The number and arrangement of electrical contacts 50 can vary, and FIG. 5 is merely a schematic representation of an embodiment. The electrical contacts 50 may be connected via electrical conduits 52 (e.g., wires) that also connect the electrical contacts 50 to the processor (not shown). The electrical contacts 50 may be arranged along the TCO coating 54. In operation, resistance between the electrical contacts 50 can be stored in memory as the established baseline of the windshield 12 having no crack. When the windshield 12 is impacted and a crack 14 is formed, electrical resistance between the electrodes in the area of the crack 14 will change compared to the established baseline. This is exemplified in FIG. 5 with two electrodes (labeled "1" and "2") adjacent the crack 14. The electrical resistance between these two electrodes will change substantially more than any change in electrical resistance between two other electrodes that are further away from the crack 14. This is exemplified in FIG. 6, where one or more electrical contacts 50 in the array of electrical contacts will show a change in signal relative to the established baseline. As such, the system can localize the crack 14. The processor can identify the specific electrical contacts that are detecting a change in the electrical resistance, and then access memory (e.g., a lookup table) that correlates the identified electrodes with a particular location on the windshield. The processor and its associated systems can, in turn, inform the driver of the location of the crack 14 based on which ones of the electrodes are detecting a disturbance in electrical resistance, or the largest change in electrical resistance amongst all of the electrical contacts 50. This is especially beneficial for smaller cracks that may be hard for the driver to see with the naked eye, allowing the driver to swiftly identify the cracks and repair or remedy the crack.

Figure 7:
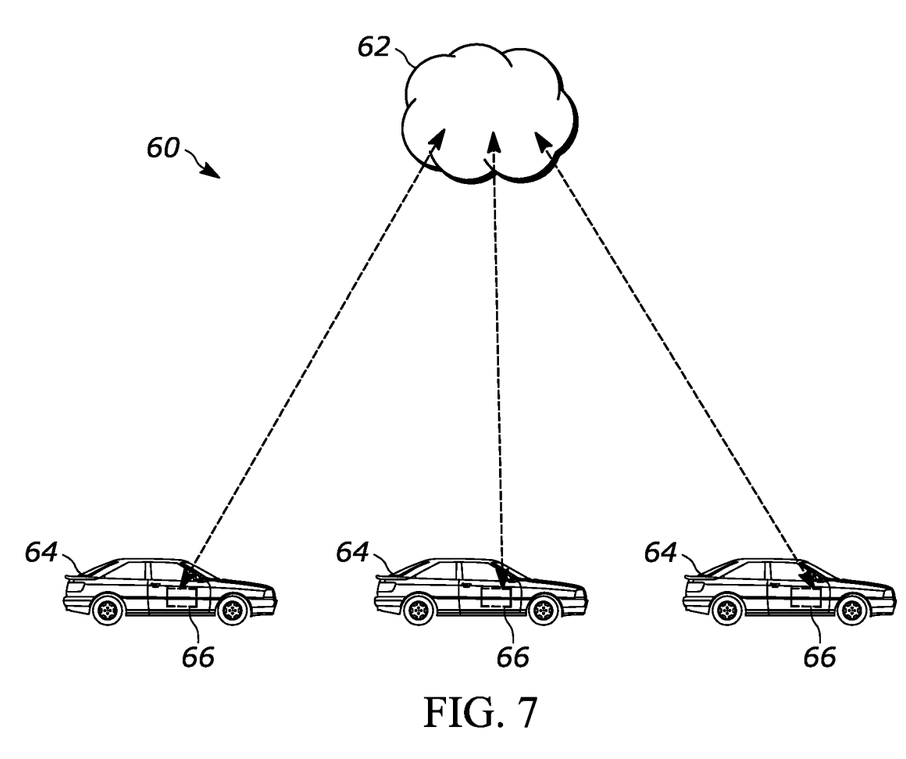
FIG. 7 is a schematic of a vehicle-to-cloud (V2C) communication system according to an embodiment.

The systems disclosed herein can rely on cloud computing for offsite processing of vehicle data from the emitters and detectors, and for remote instructions sent back to the vehicle or to a user regarding the presence of a crack in the windshield. Remote processing also allows for better machine learning capabilities by processing data from a plurality (e.g. thousands) of vehicles. FIG. 7 is a schematic illustration of a system 60 for processing data at an offsite server (e.g., the cloud 62) that is communicatively connected to a plurality of vehicles 64. The system 60 can be referred to as a vehicle-to-cloud (V2C) system. Each vehicle 64 has a communication system 66 including, but not limited to, a processor (e.g., processor 20), receiver, transceiver (e.g., transceiver 23), transmitter, and the like that is capable of receiving data from the detectors 18, transmitting the data (or a processed or pre-processed form of the data) to the offsite server, whereupon the offsite server can process the data and send corresponding processed data or instructions (e.g., an instruction to notify the user of a crack in the windshield) back to the communication system 66 to cause a message to be displayed or otherwise sent to the user regarding the presence of a crack in the windshield.

Figure 8:
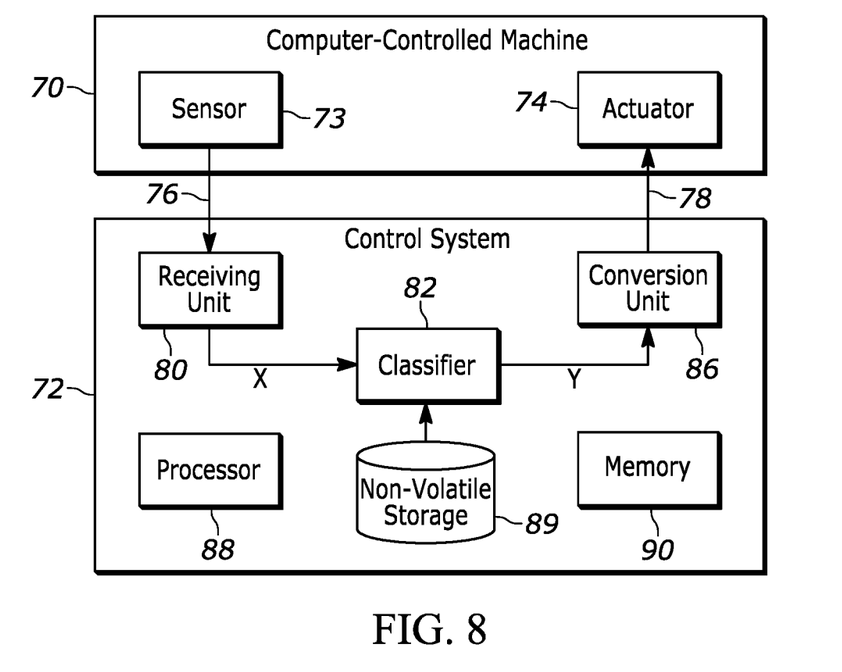
FIG. 8 is a schematic diagram of an interaction between a computer-controlled machine and a control system according to an embodiment.

FIG. 8 illustrates a schematic diagram of an interaction between a computer-controlled machine 70 and a control system 72 according to an embodiment. The computer-controlled machine 70 may be one or more of the vehicles (e.g., vehicle 66) subject to the crack detection systems described herein. The control system 72 may be a remote server. The control system 72 may be located at least partially within the cloud or remote server. The control system 72 may be located entirely at the remote server, wherein the computer-controlled machine 70 merely relays data for processing and execution at the remote server, and in turn, the remote server relays control signals to the computer-controlled machine 70 based on the processed data. It should be understood that FIG. 8 is merely a schematic illustration and is but one example of a possible layout of signal flow. This is not intended to be limiting on the scope of this disclosure unless expressly noted. The computer-controlled machine 70 and the control system 72 may all be located within the same vehicle, or may at least partially utilize or incorporate an off-site server such as the cloud; FIG. 8 is not intended to limit the system 10 to any one type of layout of data detection, computation, and control.

The computer-controlled machine 70 includes sensor 73 and actuator 74. The sensor 73 and actuator 74 may be within the same physical unit (e.g., the vehicle), or may be in different physical units (e.g., the sensor 73 within the vehicle and the actuator 74 being the mobile device of the user). The sensor 73 may include one or more of the detectors disclosed herein such as detector 18, electrode 50, and the like. The actuator 74 may include one or more actuators. Sensor 73 may be configured to encode the sensed condition into sensor signals 76 and to transmit sensor signals 76 to control system 72 either directly or indirectly via the communication capabilities disclosed herein.

Control system 72 is configured to receive sensor signals 76 from computer-controlled machine 70. As set forth below, control system 72 may be further configured to compute actuator control commands 78 depending on the sensor signals 76 and to transmit actuator control commands 78 to actuator 74 of computer-controlled machine 70. In one general example, the control system 72 is configured to send an actuator control command 78 informing an actuator 74 (e.g., a vehicle display) to display a notification based on signal processing indicating a crack in the windshield; the actuator 74 would in turn display the notification based on the actuator control command 78. In another general example, the actuator 74 includes a system for sending notifications and/or scheduling an authorized technician to service the vehicle to diagnose and fix the windshield causing the alarm. In particular, the actuator 74 may include a scheduling event being created to the vehicle owner and/or a service technician for coming to the vehicle. This will result in service technicians and vehicle owners being notified of a problem (e.g., crack in the windshield) even before the vehicle owner might visually detect the presence of the crack.

As shown in FIG. 8, the control system 72 includes receiving unit 80, or receiver. Receiving unit 80 may be configured to receive sensor signals 76 from sensor 73 (e.g., indirectly or directly from transceiver 23) and to transform sensor signals 76 into input signals x. In an alternative embodiment, sensor signals 76 are received directly as input signals x without receiving unit 80. Each input signal x may be a portion of each sensor signal 76. Receiving unit 80 may be configured to process each sensor signal 76 to produce each input signal x. Input signal x may include data corresponding to the signatures of the signals as detected by sensor 73.

Control system 72 includes classifier 82. Classifier 82 may be configured to classify input signals x into one or more labels using a machine learning (ML) algorithm, such as a neural network. In one embodiment, the classifier 82 is configured to classify input signals x into one or more labels using a crack detection machine learning model. Classifier 82 is configured to be parameterized by parameters $\theta$. Parameters $\theta$ may be stored in and provided by non-volatile storage 84. Classifier 82 is configured to determine output signals y from input signals x. Each output signal y includes information that assigns one or more labels to each input signal x. Classifier 82 may transmit output signals y to conversion unit 86. Conversion unit 86 is configured to covert output signals y into actuator control commands 78. Control system 72 is configured to transmit actuator control commands 78 to actuator 74 (either directly or indirectly via, for example, the transceiver 23), which is configured to actuate computer-controlled machine 70 in response to actuator control commands 78. In another embodiment, actuator 74 is configured to actuate computer-controlled machine 70 based directly on output signals y. As an example, the classifier 82 may be configured to classify input signals x as either "normal" or "abnormal" based upon the learned models and classifiers disclosed herein. For example, learned input signals indicating a sensor signature may be classified as normal, while signal signatures deviating from the learned normal by a threshold may be classified as abnormal. When input signals are classified as abnormal, the system may send an output signal y causing a notification or action to remedy the potential issue with the windshield, according to embodiments described herein.

Sensor signals 76 may be sent via the transceiver 23, and actuator control commands 78 may be received by the transceiver 23. Meanwhile, the control system 72 may have its own transceiver or receiver (such as including receiving unit 80) for sending and receiving sensor signals 76 and actuator control commands 78.

Upon receipt of actuator control commands 78 by actuator 74, actuator 74 is configured to execute an action corresponding to the related actuator control command 78. Actuator 74 may include a control logic configured to transform actuator control commands 78 into a second actuator control command, which is utilized to control actuator 74. In one or more embodiments, actuator control commands 78 may be utilized to control a display instead of or in addition to an actuator; the actuator may cause the I/O interface 21 to display a message regarding a presence of the crack.

As shown in FIG. 8, control system 72 also includes processor 88 and memory 90. Processor 88 may include one or more processors. Memory 90 may include one or more memory devices. The classifier 82 (e.g., ML algorithms such as crack detection machine learning model) of one or more embodiments may be implemented by control system 72, which includes non-volatile storage 84, processor 88 and memory 90.

Non-volatile storage 84 may include one or more persistent data storage devices such as a hard drive, optical drive, tape drive, non-volatile solid-state device, cloud storage or any other device capable of persistently storing information. Processor 88 may include one or more devices selected from high-performance computing (HPC) systems including high-performance cores, microprocessors, micro-controllers, digital signal processors, microcomputers, central processing units, application specific integrated circuit, field programmable gate arrays, programmable logic circuit, state machines, analog circuits, digital circuits, or any other devices that manipulate signals (analog or digital) based on computer-executable instructions residing in memory 90. Memory 90 may include a single memory device or a number of memory devices including, but not limited to, random access memory (RAM), volatile memory, non-volatile memory, static random access memory (SRAM), electrically erasable programmable ROM (EEPROM), dynamic random access memory (DRAM), flash memory, cache memory, or any other device capable of storing information.

Processor 88 may be configured to read into memory 90 and execute computer-executable instructions residing in non-volatile storage 84 and embodying one or more machine learning algorithms and/or methodologies of one or more embodiments described herein, such as the crack detection machine learning model. Non-volatile storage 84 may include one or more operating systems and applications. Non-volatile storage 84 may store compiled and/or interpreted from computer programs created using a variety of programming languages and/or technologies, including, without limitation, and either alone or in combination, Java, C, C++, C#, Objective C, Fortran, Pascal, Java Script, Python, Perl, and PL/SQL. Non-volatile storage 84 and memory 90 may more generally be referred to as storage.

Upon execution by processor 88, the computer-executable instructions of non-volatile storage 84 may cause control system 72 to implement one or more of the machine learning algorithms and/or methodologies as disclosed herein. Non-volatile storage 84 may also include machine learning data (including data parameters) supporting the functions, features, and processes of the one or more embodiments described herein.

The program code embodying the algorithms and/or methodologies described herein is capable of being individually or collectively distributed as a program product in a variety of different forms. The program code may be distributed using a computer readable storage medium having computer readable program instructions thereon for causing a processor to carry out aspects of one or more embodiments. Computer readable storage media, which is inherently non-transitory, may include volatile and non-volatile, and removable and non-removable tangible media implemented in any method or technology for storage of information, such as computer-readable instructions, data structures, program modules, or other data. Computer readable storage media may further include RAM, ROM, erasable programmable read-only memory (EPROM), electrically erasable programmable read-only memory (EEPROM), flash memory or other solid state memory technology, portable compact disc read-only memory (CD-ROM), or other optical storage, magnetic cassettes, magnetic tape, magnetic disk storage or other magnetic storage devices, or any other medium that can be used to store the desired information and which can be read by a computer. Computer readable program instructions may be downloaded to a computer, another type of programmable data processing apparatus, or another device from a computer readable storage medium or to an external computer or external storage device via a network.

Computer readable program instructions stored in a computer readable medium may be used to direct a computer, other types of programmable data processing apparatus, or other devices to function in a particular manner, such that the instructions stored in the computer readable medium produce an article of manufacture including instructions that implement the functions, acts, and/or operations specified in the flowcharts or diagrams. In certain alternative embodiments, the functions, acts, and/or operations specified in the flowcharts and diagrams may be re-ordered, processed serially, and/or processed concurrently consistent with one or more embodiments. Moreover, any of the flowcharts and/or diagrams may include more or fewer nodes or blocks than those illustrated consistent with one or more embodiments.

The processes, methods, or algorithms can be embodied in whole or in part using suitable hardware components, such as Application Specific Integrated Circuits (ASICs), Field-Programmable Gate Arrays (FPGAs), state machines, controllers or other hardware components or devices, or a combination of hardware, software and firmware components.

In general, the classifier 82 and/or the windshield crack detection machine learning model is trained to learn a function that provides a precise correlation between input values and output values. At runtime, a machine learning engine uses the knowledge encoded in the machine learning model or classifier 82 against observed data to derive conclusions such as a diagnosis or a prediction. It is contemplated that the machine-learning algorithm may employ known machine-learning classification algorithms like linear classifiers, support vector machines, decision trees, boosted trees, random forest, neural networks, or nearest neighbor.

Figure 9:
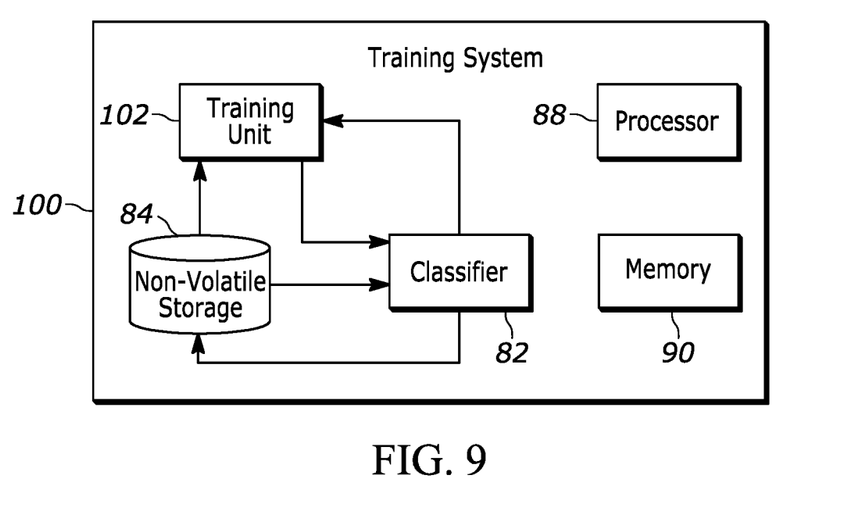
FIG. 9 is a schematic diagram of a training system for training a classifier according to an embodiment.

FIG. 9 illustrates a schematic diagram of a training system 100 for training the classifier 82 according to an embodiment. Training unit 102 is configured to determine input signals x and to transmit input signals x to classifier 82. In one embodiment, training unit 102 is configured to access non-volatile storage 84 to obtain a set of training data X={(x1, y1), . . . , (xn, yn)} stored thereon. Non-volatile storage 84 also stores a loss function L. Non-volatile storage 84 may also store a set of class-dependent allowed perturbations. Furthermore, the training system 100 may include processor 88 and memory 90. The non-volatile storage 84, processor 88, and memory 90 may each be or include similar structure as those components described above with respect to FIG. 8. Alternatively, one or more of the non-volatile storage 84, processor 88, and memory 90 may be a different unit than that of FIG. 8, albeit with structure similar to the examples described above. The machine learning algorithms of one or more embodiments may be implemented by training system 100, which includes non-volatile storage 84, processor 88 and memory 90.

In general, training system 100 is configured to provide the machine learning algorithm(s) with training data to learn from. The training data contains sample input data and a correct answer (e.g., a target or target attribute), such as signal signatures corresponding to a normal windshield and other signal signatures corresponding to a windshield with a crack in it. The machine learning algorithm(s) finds patterns in the training data that map the input data attributes to the target, and outputs an updated machine learning model that captures these patterns. In one embodiment, the crack detection machine learning model is trained by being provided with a plurality of data runs from a plurality of vehicles or windshield. The more data runs are made available, the more the crack detection machine learning model can apply learning techniques to associate signal signatures meaning "normal operation" and other signal signatures meaning "abnormal." In the event of an abnormal determination, the actuator control commands 78 can be sent.

The data runs input in the system 100 may include data associated with each make/model of vehicle to which the corresponding sensor is associated with. Across a plurality of vehicles having a common make/model, the crack detection machine learning model would thus be trained to recognize normal and abnormal behavior of the windshields of each make/model of vehicle. This can account for sound signatures and patterns that may differ across different vehicle makes/models.

Training system 100 is configured to execute a robust training procedure P to find a solution or approximate solution to learn classifier f parameterized by θ such that a robust loss is minimized with respect to θ. The robust training procedure P may be an asymmetrical robust classifier configured to be trained by training system 100 by expanding a robust loss function to be class separable. This training results in K different robust loss functions computed over a partition of the training sets across K different classes. The final classifier parameters may be obtained by solving for the sum of the K different loss functions across the partition of the training sets.

In general, the crack detection machine learning model may be trained to recognize signal signatures (e.g., from detectors 18 or electrodes 50) that deviate from the norm so much as to indicate a crack in the windshield. The amount of deviation necessary to trigger any alerts to the driver may be learned via the machine learning model. Once an abnormal sensor signature is detected by the crack detection machine learning model, the system may provide a notification to the driver of the presence of a crack in the windshield according to the systems disclosed herein.

Rather than using machine learning, the system can be configured to determine a crack in the windshield using a human-programmed algorithm. In one embodiment, a physical model may be used to program the types of detected events (e.g., nonuniformity in the sensors, etc.) that would be associated with a crack. This may be computed with a finite-element method (FEM)-based computer code that models the expected signal with and without a crack in the windshield. Such a calculation may be performed onboard the vehicle utilizing the on-board processors and memory, or on a remote server (e.g., the cloud). In another embodiment, the detection algorithm is configured to monitor and record when there is a sudden change in the signal (e.g., the voltage or current realized from the electrical contacts, for example) of more than a threshold (e.g., 5%, 10%, etc.) since the last measurement. Such a deviation may trigger the system to realize a crack in the windshield.

Upon installation, the system can be initialized to learn the "normal" measurements (i.e., without a crack in the windshield) for a certain length of time, such as a week. This can be uniform across all cars of a specific make, model, and year. Furthermore, anonymized data can be fed to the cloud. Additionally, when an event occurs or after a crack is repaired, the user or mechanic can activate a learning mode to learn the new normal measurements. Thereafter, measurements can be taken on a given time cycle (e.g., every minute, hour, or day) to continuously monitor for a crack.

Figure 10:
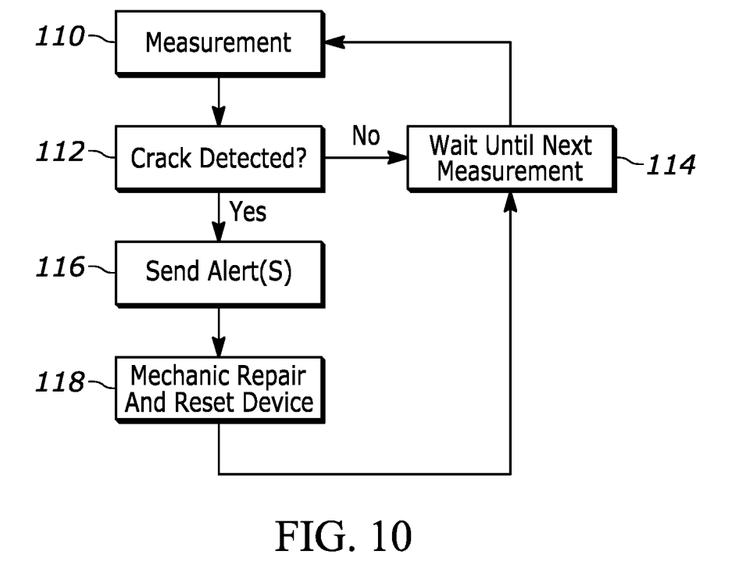
FIG. 10 illustrates a flow chart of a computational method for detecting a crack in the windshield and alerting a user of the same, according to an embodiment.

FIG. 10 illustrates a flowchart of an algorithm that can be implemented by the one or more processors described herein. At 110, a measurement is taken by one or more of the sensors 73, which can include the detectors and/or electrodes described herein. The measurements from the sensors 73 can be transmitted to a remote server such as the cloud. Data can be organized or filtered such that it can be retrieved per make/model of vehicle, for example. This allows the system to establish a "normal" windshield with no crack present via the training of the crack detection machine learning model. Likewise, this allows the machine learning model to recognize whether a signal from one or more of the sensors 73 is outside of the established norm, which may trigger the system to detect a crack at 112. The crack may be detected due to a change in the signals detected by the detectors, for example, due to the presence of the crack on the windshield. For example, sound waves or light may alter from their normal trajectory and amplitude due to the crack.

If no crack is detected—e.g., if the readings from the sensors 73 output data that is within the established normal operation measurements as determined by the crack detection machine learning model—then the system merely waits until a next measurement at 114. The system returns to 110 for another measurement.

If a crack is detected, then at 116 the system sends an alert to the driver or associated smartphone or other device of the user as described above. The alert may be sent via SMS, email, phone call, push notification, light or sound on the dashboard, infotainment system, vehicle display, and the like. The alert may also be sent to a technician, informing the technician of a potential repair or at least inspection of the windshield. The alert can also include information as to the location of the crack as detected by the methods described above.

At 118, a mechanic can assess the windshield and make any repairs as necessary. The mechanic can then reset the system (e.g., via I/O interface 21, OBD-II, etc.) such that the alert is removed and the sensory system is reset. At that time, the system can emit new signals and detect the signals via detectors to assure the detected signals are once again within the established norm so as to not trigger an alert.

The teachings herein are applicable for automotive windshields, e.g., windshields on cars, vans, trucks, sports-utility vehicles, and the like. The teachings herein can also be applicable for aviation (e.g., aircraft windshields), motorcycles (e.g., motorcycle windshields or helmet visors), and the like.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the invention that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to cost, strength, durability, life cycle cost, marketability, appearance, packaging, size, serviceability, weight, manufacturability, ease of assembly, etc. As such, to the extent any embodiments are described as less desirable than other embodiments or prior art implementations with respect to one or more characteristics, these embodiments are not outside the scope of the disclosure and can be desirable for particular applications.

What is claimed is:

1. A method of detecting a crack in a windshield and notifying a user regarding the crack, the method comprising:
    emitting a first plurality of signals across at least a portion of the windshield from emitters located at a first region of the windshield;
    detecting the first plurality of signals via detectors located at a second region of the windshield;
    processing the first plurality of signals received by the detectors to derive first signal signatures;
    storing the first signal signatures in memory;
    emitting a second plurality of signals from the emitters;
    detecting the second plurality of signals via the detectors;
    processing the second plurality of signals received by the detectors to derive second signal signatures;
    comparing the second signal signatures with the first signal signatures; and
    notifying a user regarding a presence of a crack in the windshield in response to the second signal signatures deviating from the first signal signatures.

2. The method of claim 1, wherein the emitters are optical emitters such that the steps of emitting include emitting light.

3. The method of claim 2, further comprising orienting the optical emitters such that the light travels through total internal reflection (TIR) within the windshield.

4. The method of claim 1, further comprising:
    attaching the emitters along a first edge of the windshield; and
    attaching the detectors along a second edge of the windshield opposite the first edge.

5. The method of claim 1, wherein the emitters are acoustic emitters such that the steps of emitting include emitting sound.

6. The method of claim 5, wherein the detectors are acoustic detectors, the method further comprising embedding the detectors in an array throughout the windshield.

7. The method of claim 1, further comprising:
    disposing the detectors in an array throughout the windshield;
    determining a location of the crack based upon which of the detectors detect the second plurality of signals corresponding to the second signal signatures that deviate from the first plurality of signal signatures.

8. The method of claim 1, further comprising:
    storing a plurality of signal signatures from a plurality of vehicles into the memory; and
    classifying the second signal signatures using a machine learning model using the plurality of signal signatures stored in the memory.

9. The method of claim 1, further comprising:
    coating a portion of the windshield with a transparent conducting oxide (TCO) with the detectors disposed along the TCO.

10. The system method of claim 9, wherein the transparent conducting oxide includes at least one of the following:
    $M_xZnO_{1+y}$ where M=Al and/or Ga, x is between 0 and 1, and y is between −1 and 1;
    $M_xTiO_{2+y}$ wherein M=Sb and/or W, x is between 0 and 1, and y is between −1 and 1; and
    $M_xSnO_{2+y}$ wherein M=Sb, F, and/or In; x is between 0 and 1, and y is between −1 and 1.

* * * * *